US006306373B1

(12) United States Patent
Impernate et al.

(10) Patent No.: US 6,306,373 B1
(45) Date of Patent: Oct. 23, 2001

(54) MIXED N-BUTYL AND ISO-PROPYL PHTHALAMIDE COMPOUNDS AS SUNSCREEN SOLUBILIZERS

(75) Inventors: John Impernate, Califon, NJ (US); Anthony J. O'Lenick, Jr., Dacula, GA (US)

(73) Assignee: Phoenix Research Corporation, Somerville, NJ (US)

( * ) Notice: Subject to any disclaimer, the term of this patent is extended or adjusted under 35 U.S.C. 154(b) by 0 days.

(21) Appl. No.: 09/640,069

(22) Filed: Aug. 17, 2000

(51) Int. Cl.[7] .................. A61K 7/42; A61K 7/44; A61K 7/00
(52) U.S. Cl. ............ 424/59; 424/60; 424/400; 424/401
(58) Field of Search ................ 424/59, 60, 400, 424/401

(56) References Cited

U.S. PATENT DOCUMENTS 5,204,090    4/1993    Sie-ta .

*Primary Examiner*—Shelley A. Dodson

(57) ABSTRACT

The present invention is directed to a high active sunscreen composition for topical application to human skin to protect the skin against UV radiation damage. The composition is particularly suitable for over-coating with make-up or other cosmetic compositions. More particularly, the present invention is directed to the use of a specific eutectic mixture of lower alkyl phthalamide that is surprisingly effective in solubilizing 4-(1,1-dimethylethyl)-4'-methoxydibenzoylmethane (PARSOL.RTM. 1789). Such concentrates solutions of PARSOL.RTM. 1789 can be used to formulate a more effective sunscreen, having a surprisingly increased sunscreen protection factor (SPF) and such that the PARSOL.RTM. 1789 is more effective over a longer period of time so that the sunscreen composition need not be applied to the skin as frequently.

8 Claims, No Drawings

MIXED N-BUTYL AND ISO-PROPYL PHTHALAMIDE COMPOUNDS AS SUNSCREEN SOLUBILIZERS

FIELD OF THE INVENTION

The present invention is directed to a high active sunscreen composition for topical application to human skin to protect the skin against UV radiation damage. The composition is particularly suitable for over-coating with make-up or other cosmetic compositions. More particularly, the present invention is directed to the use of a lower alkyl phthalamide that is surprisingly effective in solubilizing 4-(1,1-dimethylethyl)-4'-methoxydibenzoylmethane (PARSOL.RTM.1789). Such concentrates solutions of PARSOL.RTM. 1789 can be used to formulate a more effective sunscreen, having a surprisingly increased sunscreen protection factor (SPF) and such that the PARSOL.RTM. 1789 is more effective over a longer period of time so that the sunscreen composition need not be applied to the skin as frequently.

DESCRIPTIONS OF THE ARTS AND PRACTICES

It is well known that ultraviolet light having a wavelength between about 280 nm or 290 nm and 320 nm (UV-B) is harmful to human skin, causing burns that are detrimental to the development of a good sun tan. UV-A radiation, while producing tanning of the skin, also can cause damage, particularly to very lightly color, sensitive skin, leading to reduction of skin elasticity and wrinkles.

Therefore, a sunscreen composition should include both UV-A and UV-B filters to prevent most of the sunlight within the full range of about 280 nm to about 400 nm from damaging human skin.

The UV-B filters that are most widely used commercially in sunscreen compositions are paramethoxycinnamic acid esters, such as 2-ethylhexyl paramethoxycinnamate, commonly referred to as octyl methoxycinnamate or ARSOL.RTM. MCX, having an ethyl radical extending from the 2 position of the hexyl long chain backbone; and octyl salicylate.

A very desirable UV-A filter is 4-(1,1-dimethylethyl)-4'-methoxydibenzoylmethane (sold commercially as PARSOL.RTM. 1789). Sunscreens are commonly used as emulsions, that is a water phase into which is dispersed the sunscreen active in a suitable oil phase. It is also well known that is 4-(1,1-dimethylethyl)-4'-methoxydibenzoylmethane suffers from insolubility in a variety of solvents, commonly esters, requiring the use of large amounts of ester and a large concentration of oil phase in the sunscreen. The presence of the ester does not contribute to sunscreen efficiency, is costly and changes the skin feel of the emulsion applied to the skin. Additionally, the presence of the large concentration of ester results in several formulating problems for the chemist making sunscreens. One of these problems is that the ester used can result in a large organic loading of the emulsion and require large amounts of preservatives to keep bacteria from attacking the ester present as a solvent. The best solution would be to develop a formulation in which the oil phase has a high concentration of 4-(1,1-dimethylethyl)-4'-methoxydibenzoylmethane and a low concentration of solvent. Before the present invention, the amount of 4-(1,1-dimethylethyl)-4'-methoxydibenzoylmethane that could be solubilized was quite limited. The use of the lower alkyl phthalamide compounds as sunscreen solubilizers address this very problem, a long felt need in the sunscreen market.

In accordance with the principles of the present invention, it has been found, quite surprisingly, that by using very specific ranges of mixed n-butyl and iso-propyl phthalamide compounds of the present invention, very high concentrations of UV-A dibenzyolmethane derivative, particularly PARSOL.RTM. 1789, or EUSOLEX 8020, the dibenzyolmethane derivative is solubilized resulting heretofore unattainable emulsions.

SUMMARY OF THE INVENTION

In brief, the present invention is directed to sunscreen compositions made up of a solution of 40% to 70% by weight of 4-(1,1-dimethylethyl)-4'-methoxydibenzoylmethane (PARSOL.RTM. 1789), and 30% to 60% by weight of a mixture of n-butyl, isopropyl phthalamide compound conforming to the following structure;

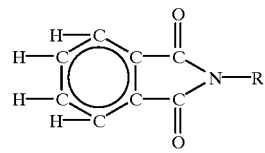

wherein;

R is a eutectic mixture having 60–75% by weight of $CH_3—(CH_2)_3—$ and 25%–40% by weight of 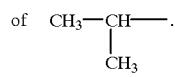

The material is a mixture of the above alkyl groups. By making the specified mixtures of the alkyl groups, most importantly normal butyl and isopropyl, a so-called eutectic mixture results. This mixture is a liquid having a very low melting point and remains liquid over a wide range of temperatures. We have found that the increased solubilization of the sunscreen compounds in the mixture occurs only within the so-called eutectic range. Within the eutectic rang, a mixture of the compounds has a lower melting point than either of the two pure components in the mixture. We have discovered that this phenomenon is critically important in developing compounds that can solubilize high levels of sunscreening agents.

Surprisingly, the key to solubilizing large quantities of sunscreen is the selection of the aromatic, amid functional lower alkyl compounds. The industry has long recognized the need for efficient solubilizers, but has looked at esters. The ester class of compounds provides only minimal solubility, making their use difficult. The art as a whole taught away from the use of compounds other than esters and certainly did not anticipate the properties of the specific aromatic cyclic amides of the present invention. U.S. Pat. Nos. 5,783,173, 5,788,954, and 5,849,273 incorporated herein by reference teach that the optimum solubility of the specific sunscreens (avobenzone) in esters is 13% by weight at best. This means the oil phase must be present at a concentration of 87% by weight. As will become clear the compounds of the present invention will allow for the solubilization of 40% avobenzone by weight.

The above and other aspects and advantages of the present invention will become more apparent from the following detailed description of the preferred embodiments.

Preferred Embodiment

In a preferred embodiment R is 60% by weight CH$_3$—(CH$_2$)$_3$— and 40% by weight of CH$_3$—CH—.
         |
         CH$_3$ In a preferred embodiment R is 62% by weight CH$_3$—(CH$_2$)$_3$— and 38% by weight of CH$_3$—CH—.
         |
         CH$_3$ In a preferred embodiment R is 65% by weight CH$_3$—(CH$_2$)$_3$— and 35% by weight of CH$_3$—CH—.
         |
         CH$_3$ In a preferred embodiment R is 67% by weight CH$_3$—(CH$_2$)$_3$— and 33% by weight of CH$_3$—CH—.
         |
         CH$_3$ In a preferred embodiment R is 70% by weight CH$_3$—(CH$_2$)$_3$— and 30% by weight of CH$_3$—CH—.
         |
         CH$_3$ In a preferred embodiment R is 72% by weight CH$_3$—(CH$_2$)$_3$— and 28% by weight of CH$_3$—CH—.
         |
         CH$_3$ In a preferred embodiment R is 75% by weight CH$_3$—(CH$_2$)$_3$— and 25% by weight of CH$_3$—CH—.
         |
         CH$_3$

EXAMPLES

Raw Materials n-butyl amine and iso-propyl amine are items of commerce and are available from a variety of sources.

|  | n-butyl amine | iso-propyl amine |
|---|---|---|
| Example 1 | 60 | 40 |
| Example 2 | 62 | 38 |
| Example 2 | 65 | 35 |
| Example 4 | 67 | 33 |

-continued

|  | n-butyl amine | iso-propyl amine |
|---|---|---|
| Example 5 | 70 | 30 |
| Example 6 | 72 | 28 |
| Example 7 | 75 | 25 |

Example 8

Phthalic Anhydride

Phthalic anhydride is an item of commerce and conforms to the following structure;

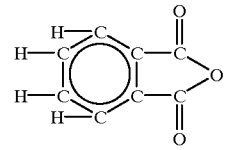

Reaction Sequence

The reaction takes place in two steps, the first at low temperatures (100–130 C.) and results in the formation of a carboxy amide.

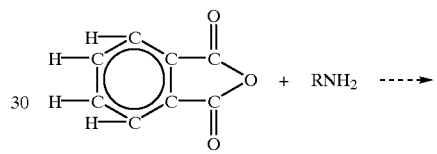

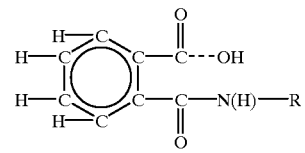

In the second step of the reaction, the amido carboxylate reacts to form a ringed structure, giving off a mole of water.

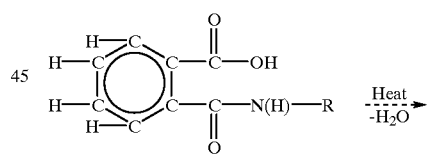

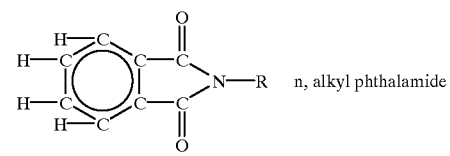 n, alkyl phthalamide

Reaction Sequence

To a suitable vessel, capable of holding pressure of 100 psig and heating the contents to 200 C. is added 146.0 grams of phthalic anhydride. The phthalic anhydride is heated to 120 C., and the reactor is sealed. Next, the specified amount of the specified amine is added over 1 hour. The reaction is somewhat exothermic. Temperature is kept between 110 and 130 C. using cooling if needed. The reaction is held for 4 hours after all the amine is added.

The pressure is relieved and the reaction mass is heated to 180–220 C. Water begins to distill off and cyclization begins. The reaction mass is held for 5 hours, then vacuum is applied to remove at least 97% of the theoretical water. The reaction mass is cooled down. The product is used with additional purification.

|  | Amine |  |
|---|---|---|
| Example | Example | Grams |
| 9 | 1 | 105.0 |
| 10 | 2 | 105.0 |
| 11 | 3 | 105.0 |
| 12 | 4 | 105.0 |
| 13 | 5 | 105.0 |
| 14 | 6 | 105.0 |
| 15 | 7 | 105.0 |

Application Examples

A study was done to determine how many grams of various solvents are necessary to solublize 1 gram of avobenzone.

| Compounds of the present invention | | |
|---|---|---|
| Material | Grams of Solvent | % Avobenzone Solution |
| Example 5 | 1.5 | 40.0 |
| Example 2 | 1.2 | 45.5 |
| Example 4 | 1.1 | 47.6 |

| Compounds of the Prior Art | | |
|---|---|---|
| Material | Grams of Solvent | % Avobenzone Solution |
| Dioctyl maleate | 4.0 | 20.0 |
| Di-isopropyl adipate | 7.0 | 12.5 |
| Castor oil | 10.0 | 9.0 |
| Decyl oleate | 10.0 | 9.0 |
| Octyldodecanol | 25.0 | 3.8 |
| Hexyl laurate | 8.0 | 11.1 |
| Isopropanol | 50.0 | 2.0 |
| Cyclomethicone | 500.0 | 0.2 |
| C12–C15 Alcohols Benzoate | 7.0 | 12.5 |

As can be easily seen, the compounds of the present invention result in heretofore unattainable levels of avobenzone, and are cosmetically elegant, having a very nice feel on the skin.

What is claimed is:

1. A sunscreen compositions made up of a solution of 40% to 70% by weight of 4-(1,1-dimethylethyl)-4'-methoxydibenzoylmethane, and 30% to 60% by weight of a mixed phthalamide compound conforming to the following structure;

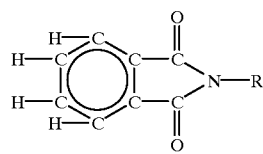

wherein;
R is a eutectic mixture having 60–75% by weight of $CH_3$—$(CH_2)_3$— and 25%–40% by weight of $CH_3$—$\underset{\underset{CH_3}{|}}{CH}$—.

2. A composition of claim 1 wherein R is 60% by weight $CH_3$—$(CH_2)_3$— and 40% by weight of $CH_3$—$\underset{\underset{CH_3}{|}}{CH}$—.

3. A composition of claim 1 wherein R is 62% by weight $CH_3$—$(CH_2)_3$— and 38% by weight of $CH_3$—$\underset{\underset{CH_3}{|}}{CH}$—.

4. A composition of claim 1 wherein R is 65% by weight $CH_3$—$(CH_2)_3$— and 35% by weight of $CH_3$—$\underset{\underset{CH_3}{|}}{CH}$—.

5. A composition of claim 1 wherein R is 67% by weight $CH_3$—$(CH_2)_3$— and 33% by weight of $CH_3$—$\underset{\underset{CH_3}{|}}{CH}$—.

6. A composition of claim 1 wherein R is 70% by weight $CH_3$—$(CH_2)_3$— and 30% by weight of $CH_3$—$\underset{\underset{CH_3}{|}}{CH}$—.

7. A composition of claim 1 wherein R is 72% by weight $CH_3$—$(CH_2)_3$— and 28% by weight of $CH_3$—$\underset{\underset{CH_3}{|}}{CH}$—.

8. A composition of claim 1 wherein R is 75% by weight $CH_3$—$(CH_2)_3$— and 25% by weight of $CH_3$—$\underset{\underset{CH_3}{|}}{CH}$—.

* * * * *

UNITED STATES PATENT AND TRADEMARK OFFICE
CERTIFICATE OF CORRECTION

PATENT NO. : 6,306,373 B1
DATED : October 23, 2001
INVENTOR(S) : Imperante et al.

It is certified that error appears in the above-identified patent and that said Letters Patent is hereby corrected as shown below:

Title page,
Item [75], Inventors's Name change "Impernate" and inset therefore -- Imperante --
Item [54], Title, change "PHTHALAMIDE" and insert therefore
-- PHTHALIMIDE --
Item [57], ABSTRACT,
Line 7, change "phthalamide" and insert therefore -- phthalimide --

Column 1,
Lines 2 and 66, change "phthalamide" and insert therefore -- phthalimide --

Column 2,
Lines 3 and 17, change "phthalamide" and insert therefore -- phthalimide --

Column 5,
Line 52, change "phthalamide" and insert therefore -- phthalimide --

Signed and Sealed this

Sixteenth Day of July, 2002

*Attest:*

JAMES E. ROGAN
*Director of the United States Patent and Trademark Office*

*Attesting Officer*